United States Patent [19]

Redbrake-Adams et al.

[11] Patent Number: 6,162,642
[45] Date of Patent: Dec. 19, 2000

[54] AGENT FOR DEHYDRATING CORNEAS IN ORGAN CULTURE

[75] Inventors: Claudia Redbrake-Adams; Martin Reim, both of Aachen, Germany

[73] Assignee: Fresenius AG, Bad Homburg, Germany

[21] Appl. No.: 09/359,374

[22] Filed: Jul. 23, 1999

Related U.S. Application Data

[63] Continuation of application No. PCT/EP98/00324, Jan. 22, 1998.

[30]    Foreign Application Priority Data

Jan. 23, 1997  [DE]  Germany .......................... 197 02 210

[51] Int. Cl.$^7$ .............................. C12N 5/00; A01N 1/00; A01N 1/02; G01N 31/00; C07H 1/06
[52] U.S. Cl. ........................... 435/325; 435/1.1; 435/1.2; 435/1.3; 436/18; 536/128
[58] Field of Search ............... 435/1.1, 1.2, 1.3, 435/325; 536/128; 436/18; 523/27, 29, 31, 32, 35–55, 336

[56]    References Cited

U.S. PATENT DOCUMENTS 5,306,711  4/1994  Andrews .
5,502,043  3/1996  Weidler et al. .

FOREIGN PATENT DOCUMENTS 30 07 913 A 1   9/1981   Germany .
39 19 729 A 1  12/1990   Germany .
   43 10974    4/1993   Germany .
38 43 958 C 2   3/1994   Germany .
197 02 210 C 2  1/1999   Germany .

OTHER PUBLICATIONS

Walkenbach et al., Current Eye Research, vol. 10, 12, pp 1129–1136. The effects of UW solution and its components on corneal thickness during and after storage, 1991.

*Primary Examiner*—Leon B. Lankford, Jr.
*Assistant Examiner*—Michele C. Flood
*Attorney, Agent, or Firm*—Corinne M. Pouliquen; Pepper Hamilton LLP

[57]    ABSTRACT

An agent for dehydrating corneas, in particular eye corneas for organ culture, contains the culture medium and as dehydrating substance hydroxyethylstarch with a mean molecular weight Mw from 070,000 to 200,000, an MS substitution degree from 0.15 to 0.5, a DS substitution degree from 0.15 to 0.5 and a C2–C6 substitution ratio at the anhydroglucose units $\leq 8$. The dehydrating substance is preferably hydroxyethylstarch with a mean molecular weight Mw 130,000±20,000, an MS substitution degree from 0.38 to 0.45, a DS substitution degree from 0.32 to 0.40 and a C2–C6 substitution ratio at the anhydroglucose units from 8 to 20. The hydroxyethylstarch is used in a concentration from 1 to 20 (weight/vol.) %, preferably from 2 to 15 (weight/vol.) %, and in particular of 7.5% (weight/vol.). Also disclosed is the use of this hydroxyethylstarch as a dehydrating substance for the organ culture of corneas, in particular eye corneas, and the use of this hydroxyethylstarch for preparing a dehydrating agent for corneas, in particular eye corneas for organ culture.

9 Claims, 7 Drawing Sheets

AGENT FOR DEHYDRATING CORNEAS IN ORGAN CULTURE

RELATED APPLICATION

This application is a continuation of International Application Number PCT/EP98/00324, filed Jan. 22, 1998, which in turn claims priorty from erman Patent Application No. 197 02 210.3, filed Jan. 23,1997, both of which are incorporated herein by reference.

TECHNICAL AREA

The present invention relates to a composition for the deswelling of integuments, in particular of keratoid integuments in organ culture, both human and animal, preferably human, keratoid integuments, in particular corneas of eyes, comprising the culture medium and a deswelling substance, and to the use of hydroxyethylstarch as deswelling substance in the organ culture of integuments, in particular keratoid integuments and especially of corneas of eyes and for preparing a composition for the deswelling of keratoid integuments, in particular or corneas of eyes, in organ culture.

PRIOR ART

Known hydroxyethylstarches, which are used in particular in the area of volume replacement and of hemodilution, have various average molecular weights $M_w$ and degrees of substitution MS (molar substitution) and DS (degree of substitution) as well as diverse substitution patterns. These characteristics are described in the literature (cf. K. Sommermeyer et al., "Klinisch verwendete Hydroxyethylstärke: Physikalisch-chemische Charakterisierung", Krankenhauspharmazie, page 271 (1987), and EP-0 402 724 B1).

By "keratoid integuments" are meant herein keratoid integuments in general, but especially the corneas of eyes. The integuments may be both of human origin and of animal origin (for example from pigs).

For illustration, the invention is described hereinafter for corneas of eyes, without restricting it thereto.

The storage of human corneas (from eyes) before transplantation is now possible for up to 4 weeks with the aid of organ culture. During this time, however, a not inconsiderable water uptake and thus swelling of the corneas occurs. The normal thickness of the cornea is about 0.5 mm. By contrast, values of up to 0.9 mm are reached during the culture. A precondition of use of the stored corneas is thus appropriate deswelling before the transplantation. This deswelling is currently carried out in all European cornea banks by adding dextran 500 to the culture medium. Concentrations between 5 and 8% are used, and the deswelling phase following the actual storage lasts 1 to 7 days.

Studies have shown that the deswelling in dextran leads to a radical deterioration in the energy-supplying metabolism of the cornea (Redbrake, C.: "Untersuchungen der Gewebebeschaffenheit der humanen Hornhaut in Abhängigkeit von Spenderkriterien und Lagerung in der Organkultur unter besonderer Berücksichtigung des energieliefernden Stoffwechsels", thesis, Aachen, 1996, Salla S. et al., Cornea 14 (5), 502–508, 1995). At the same time there is loss of endothelium, the number of layers of which is crucial for post-transplantation success. It has further been found in investigations that the large dextran molecule is taken up by the cornea after only one day and probably exerts its harmful effect in this way. However, it must be borne in mind that the osmotic effect also contributes to cell damage. Thus, as storage continues in the dextran-containing medium there is also progressive damage to the endothelium, as well as to the other layers of the cornea. The cell damage due to dextran has already been found in earlier investigations (cf. Sperling, S., Acta Ophthalmologica. Vol. 57 (1979), pages 269–276). In order to find other deswelling substances, experiments have already been carried out with hydroxyethylstarch 450, 000 (Reim. M. et al., Klin. Mbl. Augenheilk 196, pages 76080 (1990)). However, in this case there was less interest in replacing the dextran than in the aim of keeping the cornea unswollen throughout the storage in order to avoid the deswelling phase necessary before transplantation. Although these experiments showed the good osmotic effect of the hydroxyethylstarch 450,000, cleavage of the molecule resulted in a pronounced excess of saccharides in the medium, which had adverse effects on the metabolism. During organ culture in a nutrient-rich culture medium there is normally a recuperation of the metabolism of the cornea.

DESCRIPTION OF THE INVENTION

The object of the invention is to provide compositions which are suitable for keeping the cornea unswollen throughout storage or for deswelling of the stored cornea before transplantation but which do not have the disadvantageous effects of the compositions previously used.

It has surprisingly been found according to the invention that by use of hydroxyethylstarch with an average molecular weight $M_w$ of 70,000 to 200,000, with a degree of substitution MS of from 0.15 to 0.5, with a degree of substitution DS of from 0.15 to 0.5 and with a ratio of substitution at C2 to substitution at C6 of the anhydroglucose units of $\geq 8$ as deswelling substance in place of dextran, there is better deswelling of the corneas without simultaneous major damage to the endothelium, and that in addition a distinct improvement in the metabolic state of the cornea is achieved.

A suitable hydroxyethylstarch according to the invention is hydroxyethylstarch with an average molecular weight $M_w$ of from 70,000 to 200,000, with a degree of substitution MS of from 0.15 to 0.5, with a degree of substitution DS of from 0.15 to 0.5 and with a ratio of substitution at C2 to substitution at C6 of the anhydroglucose units of $\geq 8$, preferably a hydroxyethylstarch with an average molecular weight of from 100,000 to 160,000, with a degree of substitution MS of from 0.2 to 0.45, with a degree of substitution DS of from 0.2 to 0.4 and with a ratio of substitution at C2 to substitution at C6 of the anhydroglucose units of from 8 to 20. A particularly preferred hydroxyethylstarch according to the invention has an average molecular weight of 130,000±20,000 (HES 130), a degree of substitution MS of from 0.38 to 0.45, a degree of substitution DS of from 0.32 to 0.40 and a ratio of substitution at C2 to substitution at C6 of the anhydroglucose units of from 8 to 20, such as, for example, hydroxyethylstarch with an average molecular weight of 117,000, with a degree of substitution MS of 0.39, with a degree of substitution DS of 0.34, with a ratio of substitution at C2 to substitution at C6 of the anhydroglucose units of 11, hydroxyethylstarch with an average molecular weight $M_w$ 133,800, with a degree of substitution MS of 0.44, with a degree of substitution DS of 0.38, with a ratio of substitution at C2 to substitution at C6 of the anhydroglucose units of 12.4, hydroxyethylstarch with an average molecular weight $M_w$ 148,700, with a degree of substitution MS of 0.42, with a degree of substitution DS of 0.37 and with a ratio of substitution at C2 to substitution at C6 of the anhydroglucose units of 11.7.

The hydroxyethylstarch used according to the invention can be prepared by the process described in EP 0 402 724 B1 or DE 39 19 729. The disclosure in EP 0 402 724 B1 and DE 39 19 729 is incorporated herein by reference.

The composition according to the invention or the hydroxyethylstarch used according to the invention can be employed according to the invention both to keep the cornea unswollen throughout storage (long-term culture), i.e. in order to prevent swelling of the cornea from the outset, and for deswelling of the already stored and swollen cornea before transplantation.

The term "deswelling substance" or "composition for deswelling" used herein relates according to the invention both to the use for deswelling of the cornea after storage and to the use as permanent addition to the culture medium in order to keep the cornea in the unswollen state throughout storage.

The composition according to the invention comprises the particular culture medium in which hydroxyethylstarch is present.

It is suitable according to the invention to use the hydroxyethylstarch in the culture medium in concentrations of from 1 to 20% (weight/volume), with concentrations in the range from 2 to 15% (weight/volume) being preferred, and the hydroxyethylstarch being present in particular in the culture medium in a concentration of from 5 to 10% (weight/volume), for example of 7.5% (weight/volume).

In order to keep the cornea unswollen throughout storage, the hydroxyethylstarch used according to the invention is added to the culture medium suitably in a concentration of from 1 to 10% (weight/volume), preferably of from 1 to 5% (weight/volume) and in particular of from 2 to 7.5% (weight/volume).

For deswelling of the cornea which has swollen during storage before transplantation, the hydroxyethylstarch used according to the invention is added to the culture medium in a concentration of from 1 to 20% (weight/volume), preferably of from 2 to 15% (weight/volume), in particular of from 5 to 10% (weight/volume), for example of 7.5% (weight/volume).

The storage of the corneas in the culture medium takes place under ordinarily used cornea bank conditions such as, for example, at refrigerator temperatures (about 40°C.) or at temperatures in the range of 30–37°C., in open or closed culture systems.

Suitable as culture medium are all the usual known cell and tissue culture media for organ cultures of human and animal keratoid integuments. Examples of culture media suitable for corneas are TC 199 (Müller, M. C. et al. in Ophthalmic Res. 20 (1988), pages 44–53), modified TC 199 medium (Reim, M. Klin. Mbl. Augenheilk. 196 (1990), pages 76–80), MEM (minimal essential medium) (Invest Ophthalmol Vis sci 12 (1973), 176–180), modified MEM (cf., for example, Redbrake, C., thesis, Aachen, 1996, page 15; modification of MEM, for example with Earle's salts, with Hank's salts and the like). The culture medium preferably used according to the invention is MEM or modified MEM, or TC 199.

Figure 5:
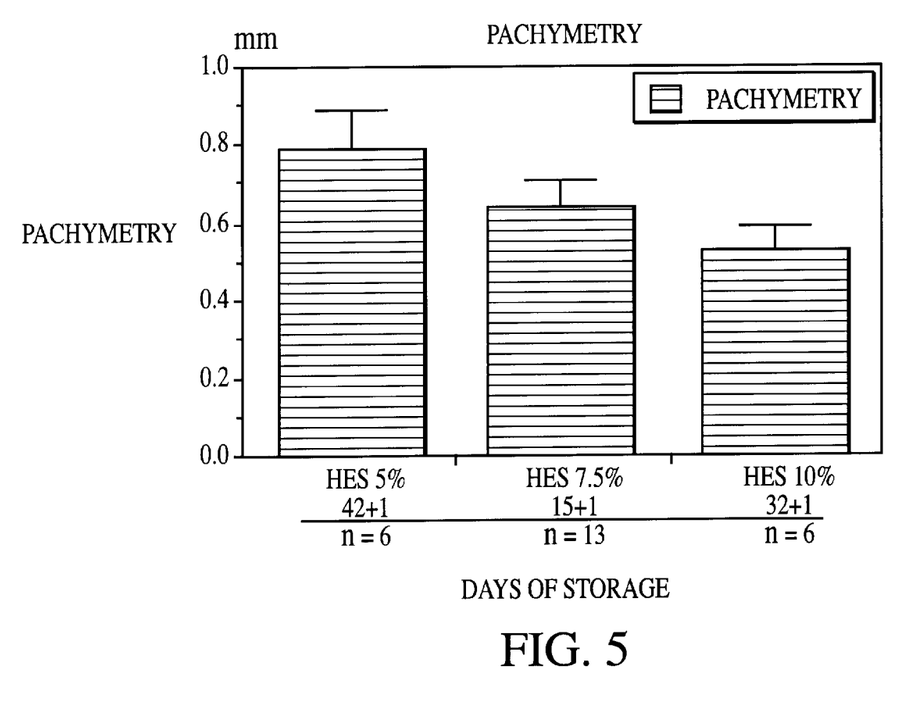
FIG. 5 illustrates the dependence of the degree of deswelling of the cornea on the concentration (in 5%, 7.5% and 10% concentration) of the HES ($M_w$ 117,000, MS 0.39, DS 0.34 and ratio of substitution at C2 to substitution at C6 of the anhydroglucose units of 11) used in the culture medium (cf. Examples 1, 2 and 3).

It has been found according to the invention that the degree of deswelling of the corneas depends on the concentration used of the hydroxyethylstarch used according to the invention, as is made clear by FIG. 5, which was produced using hydroxyethylstarch with an average molecular weight of 117,000, with an MS of 0.39, with a DS of 0.34 and with a ratio of substitution at C2 to substitution at C6 of the anhydroglucose units of 11 in 10%, 7.5% and 5% concentration in the culture medium (cf. Examples 1–3). Although the corneas were stored for various lengths of time, there is a clear dependence of the deswelling on the concentration with hydroxyethylstarch. This indicates that hydroxyethylstarch leads to uniform deswelling even where the swelling differs.

The hydroxyethylstarch used according to the invention leads to significantly better deswelling of the corneas, which is manifested by the lower pachymetry values and the lower water content, and no increase in endothelial damage. Besides the better deswelling, the hydroxyethylstarch used according to the invention provides distinctly better metabolism values and the recuperation in organ culture is not lost. In addition, a toxic effect as postulated for dextran is not found. Deswelling with the hydroxyethylstarch used according to the invention thus provides a corneal material for transplantation which is in an energetically better state than after deswelling with dextran and which is therefore also better able to survive the transplantation. Deswelling with the hydroxyethylstarch used according to the invention makes it possible to extend the storage period in a deswelling medium beyond the previous time of 4 days and also makes permanent addition as deswelling substance possible for the entire duration of the organ culture.

EXPLANATION OF THE FIGURES

FIGS. 7 to 11 likewise show the values obtained in each case after storage of the cornea in a culture medium (MEM) for 15 days.

EMBODIMENTS OF THE INVENTION

The following examples serve to illustrate the present invention. The keratoid integument employed in the examples was always the cornea of the eye.

Example 1

Use of hydroxyethylstarch (HES) with an average molecular weight $M_w$ of 117,000, with an MS of 0.39, with a DS of 0.34, with a ratio of substitution at C2 to substitution at C6 of the anhydroglucose units of 11 in 10% concentration in the culture medium. 3 human corneas underwent deswelling in the culture medium which contained 10% (weight/volume) of hydroxyethylstarch for one day. These corneas had previously been stored under cornea conditions in the culture medium without added HES for 32 days. Maximum swelling is usually reached after 14 days so that the results are comparable with longer storage periods. On use of the 10% hydroxyethylstarch-containing culture medium for one day there was very great deswelling as evident from FIG. 1. The corneal thickness after deswelling in the hydroxy-ethylstarch-containing culture medium for one day was 0.517±0.063 mm.

The medium used was modified MEM of the following composition:

| | |
|---|---|
| 10 g | of MEM powder medium with Earle's salts |
| 10 ml | of penicillin/streptomycin |
| 1 ml | of amphotericin B |
| 100 ml | of fetal calf serum |
| 3.57 g | of HEPES buffer |
| pH | adjusted to pH 7.2 with NaHCO$_3$ |
| ad 1 l | double-distilled water. |

For the hydroxyethylstarch-containing medium, 100 g of hydroxyethylstarch were added per liter of the modified MEM (i.e. 10%).

The storage conditions were as follows:

100 ml of the medium in glass bottles with a capacity of 150 ml, closed system, storage temperature 31° C.

The MEM powder medium with Earle's salts used contained the following ingredients (in mg/l in each case):

| Amino acids | | | |
|---|---|---|---|
| L-Alanine | 8.9 | L-Lysine | 73.0 |
| L-Arginine × HCL | 126.0 | L-Methionine | 15.0 |
| L-Aspartic acid | 13.3 | L-Phenylalanine | 32.0 |
| L-Asparagine | 12.3 | L-Proline | 11.5 |
| L-Cystine | 24.0 | L-Serine | 10.5 |
| L-Glutamine | 292.0 | L-Threonine | 48.0 |
| L-Glutamic acid | 14.7 | L-Tryptophan | 10.0 |
| Glycine | 7.5 | L-Tyrosine | 36.0 |
| L-Histidine × HCl × H$_2$O | 42.0 | L-Valine | 46.0 |
| L-950 Leucine | 52.5 | L-Isoleucine | 52.4 |
| Inorganic salts | | | |
| CaCl$_2$ anhydrous | 200 | | |
| KCl | 400 | | |
| MgSO$_4$ × 7 H$_2$0 | 200 | | |
| NaCl | 6800 | | |
| NaHCO$_3$ | 2200 | | |
| NaH$_2$PO$_4$ | 140 | | |
| Vitamins | | | |
| Choline chloride | 1 | | |
| Folic acid | 1 | | |
| i-Inositol | 2 | | |
| Nicotinamide | 1 | | |
| Pantothenic acid Ca salt | 1 | | |
| Pyridoxal HCl | 1 | | |
| Riboflavin | 0.1 | | |
| Thiamine HCl | 1 | | |
| Other components | | | |
| Glucose | 1000 | | |
| Phenol red | 10 | | |
| Individual additions | | | |
| Insulin Zn complex | 4 | | |
| EGF (epidermal growth factor) | 150 ng/l | | |
| Adenosine 5'-phosphate Na salt | 4 | | |
| Guanosine 3'-phosphate Na$_{(2)}$ salt | 4.5 | | |
| 2'-Deoxythymidine | 0.08 | | |
| Cytidine | 2.5 | | |
| Uridine | 2.5 | | |
| Vitamin A alcohol cryst. | 1 | | |

Example 2

Comparative investigations between hydroxyethylstarch with an average molecular weight $M_w$ 117,000, with an MS of 0.39, with a DS of 0.34, with a ratio of substitution at C2 to substitution at C6 of the anhydroglucose units of 11 in 5% (weight/volume) concentration in the culture medium and dextran 500 in 5% (weight/volume) concentration in the culture medium.

Figure 1:
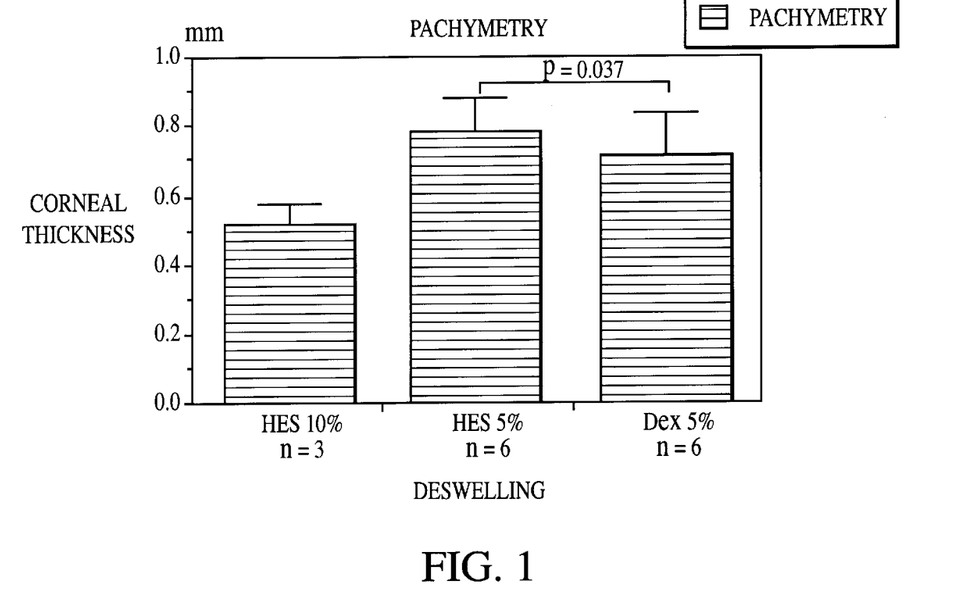
FIG. 1 relates to Examples 1 and 2 and shows the corneal thickness after deswelling with HES ($M_w$ 117,000, MS 0.39, DS 0.34 and the ratio of substitution at C2 to substitution at C6 of the anhydroglucose units of 11) in 5% and 10% concentration or with dextran 500 in 5% concentration in the culture medium for one day.
Figure 2:
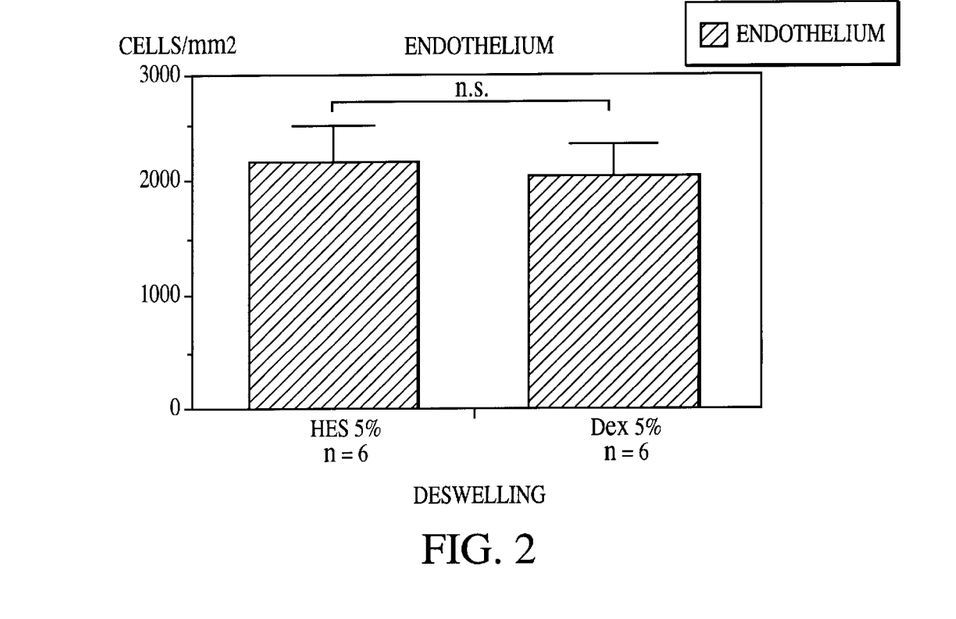
FIG. 2 relates to Example 2 and illustrates the endothelial cell levels in the corneas after deswelling with HES ($M_w$ 117,000, MS 0.39, DS 0.34 and the ratio of substitution at C2 to substitution at C6 of the anhydroglucose units of 11) and with dextran 500, each in 5% concentration in the culture medium, for one day.

These investigations were carried out as paired studies. One cornea from the same donor underwent deswelling in the culture medium containing 5% dextran 500, and the other in a medium containing 5% hydroxyethylstarch. A total of 6 pairs was investigated. The preceding culture lasted 42 days. The deswelling phase lasted 1 day. The deswelling with dextran was carried out in a standard cornea bank medium containing 10% fetal calf serum. The deswelling with hydroxyethylstarch was carried out in a standard cornea bank medium to which no calf serum was added. In these investigations, the corneal thicknesses and the endothelial cell levels were determined. The results obtained in these investigations are shown in FIGS. 1 and 2. They show a corneal thickness of 0.790±0.0969 mm for the hydroxyethylstarch-containing culture medium and a corneal thickness of 0.7253±0.1251 mm for the dextran-containing culture medium. The endothelial cell levels were 2231±296 endothelial cells per mm$^2$ for the hydroxyethylstarch-containing culture medium and 2102±283 endothelial cells per mm$^2$ for the dextran-containing culture medium.

The storage of the corneas and the determination of the corneal thickness and the endothelial cell count took place by the method described by C. Redbrake in the thesis, Aachen, 1996 "Untersuchungen der Gewebebeschaffenheit der humanen Hornhaut in Abhängigkeit von Spenderkriterien und Lagerung in der Organkultur unter besonderer Berücksichtigung des energieliefernden Stoffwechsels" (see pages 14 et seq.).

The corneas underwent pachymetry before the freeze stop using a Pach-pen (supplied by Meuter) 5 times in each case on the apex corneae. The endothelium was then photographed for documentation. This entailed taking in each case 5 photographs (1 photograph each central, top, bottom, right and left), and the endothelial cell count per mm$^2$ was determined twice on each picture.

Statistical analysis took place using the paired Student's t test and the Wilcoxon signed rank test for connected samples.

Culture medium: The culture medium used was the same medium as described in Example 1 but, to prepare the hydroxyethylstarch-containing medium, 50 g of hydroxyethylstarch were added to the modified MEM and, to prepare the dextran-containing medium, 50 g of dextran 500 were added to the modified MEM.

The storage conditions are the same as described for Example 1.

Example 3

Comparative investigations between hydroxyethylstarch with an average molecular weight $M_w$ 117,000, MS of 0.39, DS 0.34, with a ratio of substitution at C2 to substitution at C6 of the anhydroglucose units of 11 in 7.5% (weight/volume) concentration in the culture medium and dextran 500 in 5% (weight/volume) concentration in the culture medium.

Figure 3:
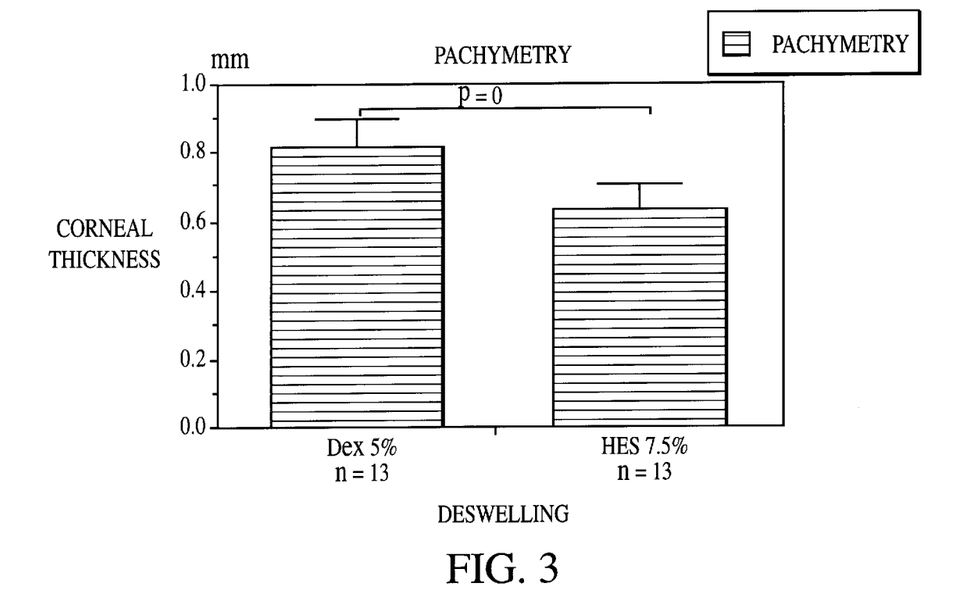
FIGS. 3 and 4 relate to Example 3 and show the corneal thickness and the endothelial cell levels after deswelling with HES ($M_w$ 117,000, MS 0.39, DS 0.34 and ratio of substitution at C2 to substitution at C6 of the anhydroglucose units of 11) in 7.5% concentration and with dextran 500 in 5% concentration in the culture medium for one day.
Figure 4:
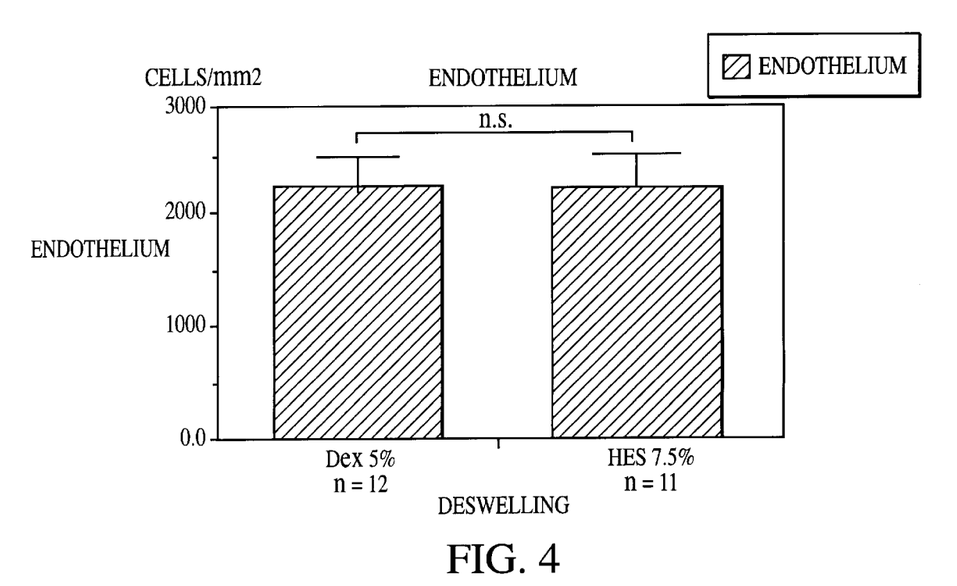

The investigation was carried out as paired study. 13 pairs were investigated therein. The culture time was 15 days and the deswelling phase only 1 day. The results obtained in these investigations are depicted in FIGS. 3 and 4. They show a significantly better deswelling with the 7.5% hydroxyethylstarch-containing culture medium (corneal thicknesses: hydroxyethylstarch-containing culture medium 0.634±0.072 mm; dextran-containing culture medium 0.805±0.085 mm) without at the same time there being correspondingly greater damage to the endothelium. The endothelial cell levels showed 2310±289 endothelial cells per mm$^2$ for the hydroxyethylstarch-containing culture medium and 2272±276 endothelial cells per mm$^2$ for the dextran-containing culture medium.

The culture medium used was the modified MEM described in Example 1 but, in the case of the hydroxyethylstarch-containing medium, the modified MEM used contained 75 g of hydroxyethylstarch (7.5% concentration) and, in the case of the dextran-containing medium, the modified MEM contained 50 g of dextran 500 (5% concentration). The conditions used corresponded to the conditions indicated in the examples mentioned above.

Example 4
Comparative Example

In the comparative study described below, hydroxyethylstarch with an $M_w$ 133, 800, with an MS of 0. 44, with a DS of 0.38 and with a ratio of substitution at C2 to a substitution at C6 of the anhydroglucose units of 12.4 in 7.5% (weight/volume) concentration in the culture medium and dextran 500 in 5% (weight/volume) concentration in the culture medium are investigated for their effect on the metabolic state of the cornea due to the deswelling compositions of the substances having a deswelling action used.

In these investigations, 12 pairs of human corneas were stored under standard conditions for 15 days. The cornea from one eye of a donor then underwent deswelling for one day in a culture medium containing 5% dextran 500, and the cornea of the other eye of the donor underwent deswelling for one day in a culture medium containing 7.5% hydroxyethylstarch (culture medium and storage conditions were the same as used in Examples 1 to 3, but with use of the HES indicated above and the dextran indicated). The biochemical investigations for quantitative determination of glucose, lactate, ATP, ADP and AMP by means of bioluminescence were then carried out. (The determination took place by the method described by C. Redbrake in the thesis, Aachen, 1996, "Untersuchungen der Gewebebeschaffenheit der humanen Hornhaut in Abhängigkeit von Spenderkriterien und Lagerung in der Organkultur unter besonderer Berücksichtigung des energieliefernden Stoffwechsels", see pages 14 et seq.). The determination, which preceded the biochemical investigations, of the wet and dry weight of the tissue allows the water content of the individual corneas to be calculated, which represents a measure of the deswelling. The normal water content of the human cornea is about 80%.

The statistical analysis of the results took place in the Stat-Works program supplied by Apple. The Man-Whitney U test was used. For the assessment, the content of glucose, lactate, ATP, ADP and AMP, and the adenylate energy charge, were determined in addition to the water content.

Nutrition of the human cornea takes place predominantly from the aqueous, from which glucose is absorbed, which is converted in the cornea by glycolysis into pyruvate and under anaerobic conditions into lactate. If much oxygen is present, it is also possible to follow the aerobic route via the citrate cycle and the respiratory chain. The ratio of anaerobic to aerobic glycolysis is 65% to 35% and is thus far over to the side of anaerobic glycolysis. This is why glucose as substrate for energy production and lactate as final product of the main metabolic pathway are important parameters for the metabolic performance of the human cornea. In the energy production by glycolysis, the cells recruit the high-energy adenosine phosphates: adenosine triphosphate (ATP), adenosine diphosphate (ADP) and adenosine monophosphate (AMP). These high-energy phosphates are required for all important cellular functions such as, for example, cell migration, cell division, active transport mechanisms etc. More adenosine phosphates present mean more functions which the cell can perform. In the cornea—as with all other tissues—the total of the adenosine phosphates also reflects the amount of cells. In contrast thereto, the adenylate energy charge is a relative parameter which describes the state of the individual cell and its energetic balance.

Figure 6:
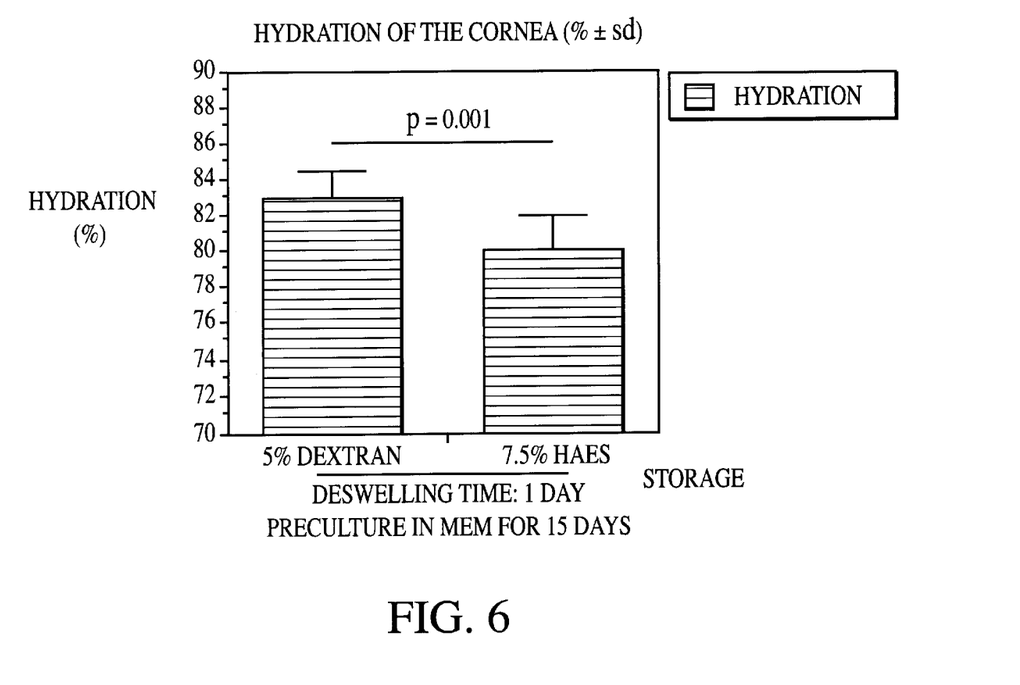
FIGS. 6 to 11 relate to Example 4 and show the results of comparative investigations with HES ($M_w$ 133,800, MS 0.44, DS 0.38 and ratio of substitution at C2 to substitution at C6 of the anhydroglucose units of 12.4) in 7.5% concentration and with dextran 500 in 5% concentration in the culture medium in relation to their effect on the metabolic state of the cornea due to deswelling for one day with the substances with a deswelling action used. These illustrate FIG. 6 the variation in hydration of the cornea, FIG. 7 the glucose content of the cornea, FIG. 8 the lactate content measured in the cornea in each case, FIG. 9 the content of ATP, ADP and AMP measured in the cornea in each case, FIG. 10 the total of the adenosine phosphates measured in the cornea and FIG. 11 the energy status of the cornea in each case.
Figure 7:
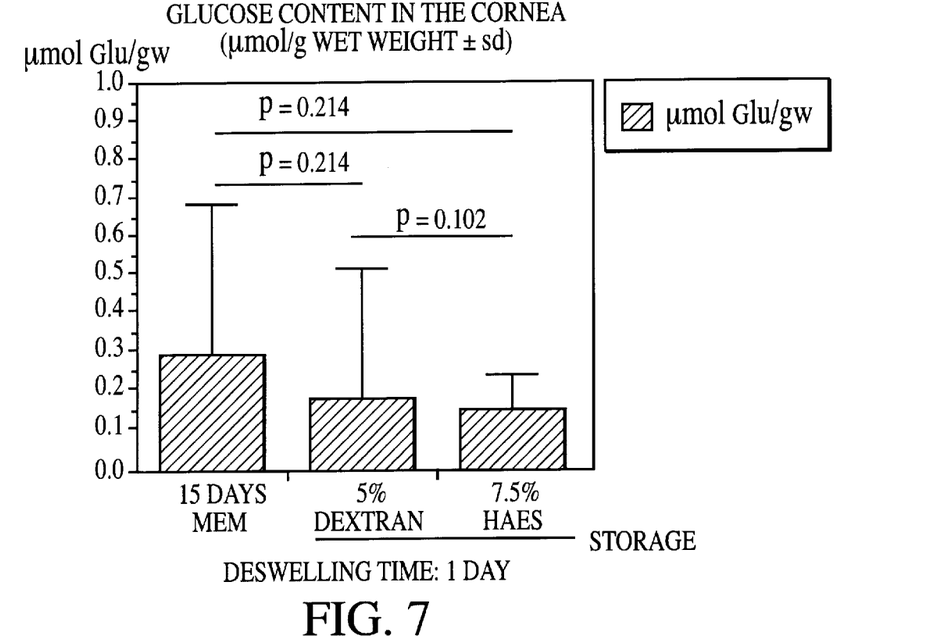
Figure 8:
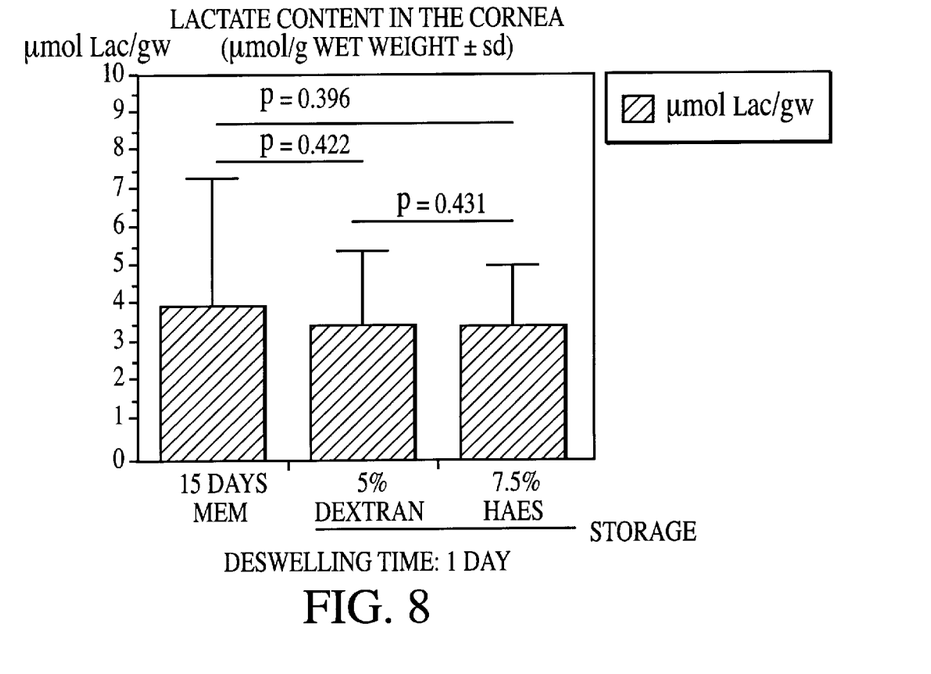
Figure 9:
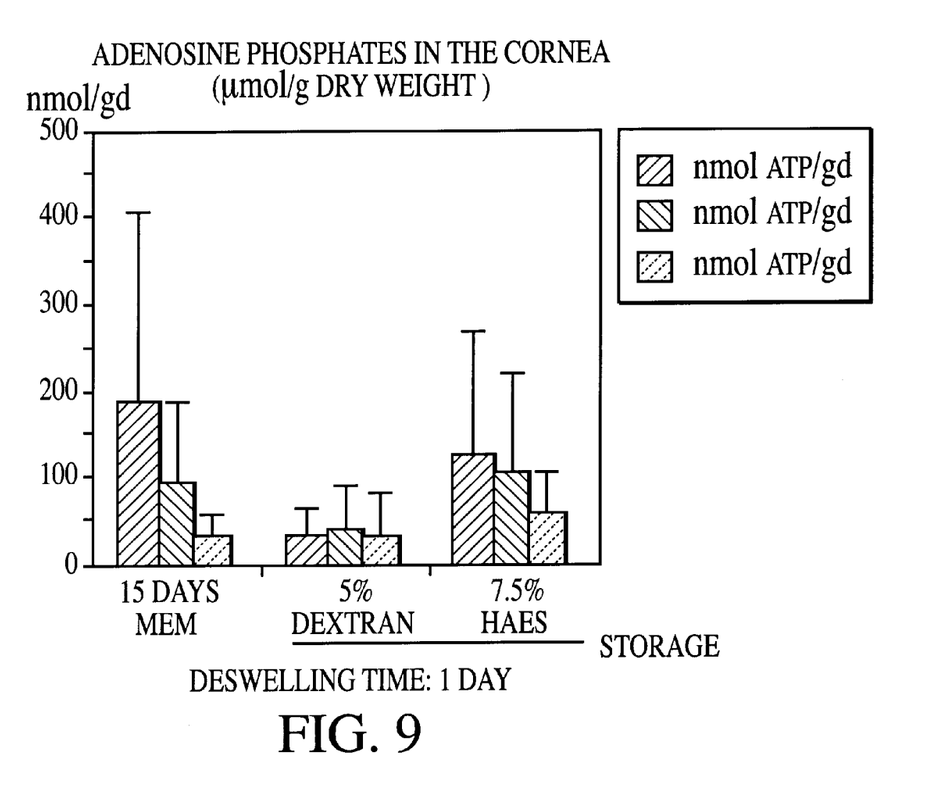
Figure 10:
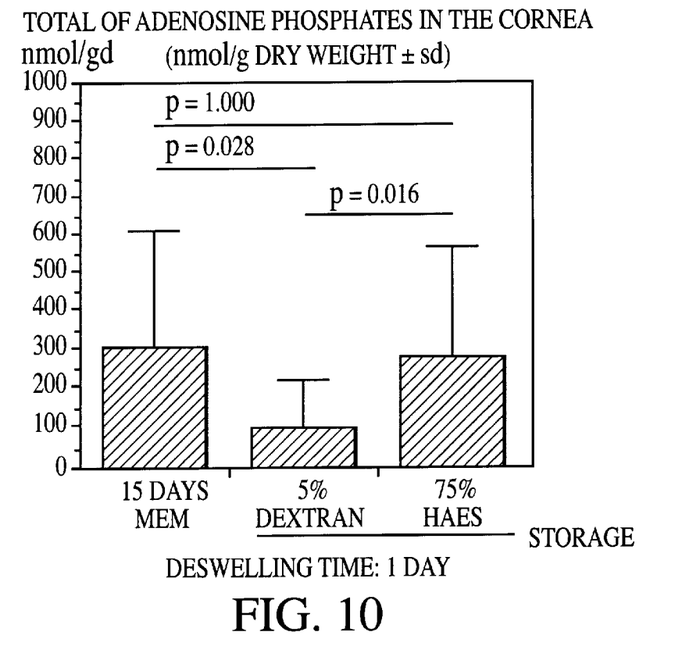
Figure 11:
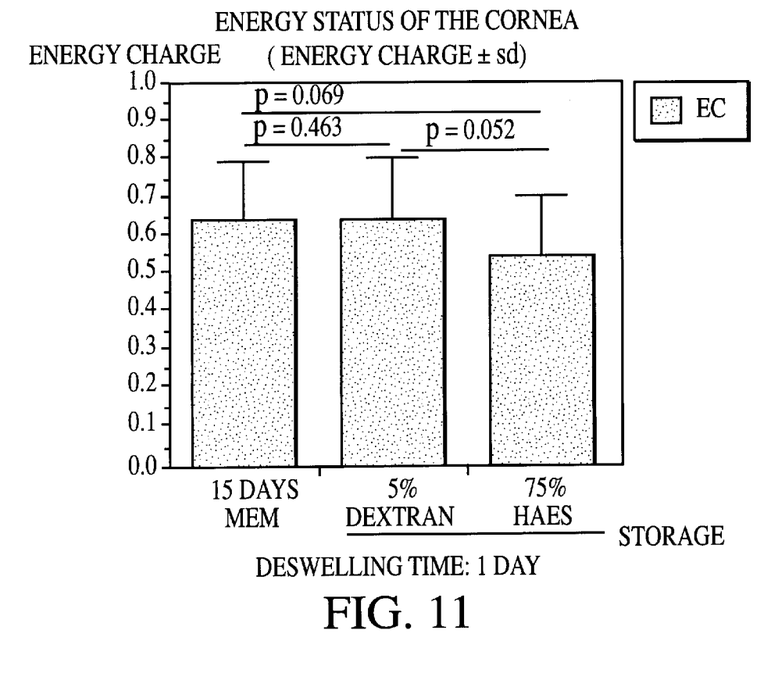

The following results were obtained in the investigations:
a) The water content of the cornea was significantly lower after deswelling with 7.5% hydroxyethylstarch (HES) than after deswelling with 5% dextran 500. The corneas deswollen with HES showed a physiological water content of 79.95%±1.83%, whereas the water content on use of dextran was 82.76±1.66% (cf. FIG. 6).
b) The deswelling led to a decrease in the glucose concentration in the corneas, by comparison with non-deswollen corneas, but the difference was not statistically significant. The standard deviation was very low for the corneas deswollen with HES by comparison with the corneas deswollen with dextran. The value for the corneas deswollen with HES was 0.159±0.085 μmol per g wet weight and for the corneas deswollen with dextran was 0.1825±0.3356 μmol per g wet weight (cf. FIG. 7).
c) The lactate levels resembled the glucose concentrations in also showing a decrease in the concentration, but this was likewise not significant. The value for the corneas deswollen with HES was 3.4896±1.6016 μmol per g wet weight and for the corneas deswollen with dextran was 3.3708±2.0025 μmol per g wet weight (cf. FIG. 8).
d) The deswelling led in every case to a decrease in ATP, but this was distinctly less pronounced in the swelling by use of HES and was not significantly different from storage for 15 days either. By contrast, on deswelling by use of dextran, statistical comparison showed a highly significant decrease in the ATP concentration. The ATP levels were significantly better on deswelling by use of HES than on deswelling by use of dextran. The value on use of HES was 124.6524 nmol per g dry weight and that on use of dextran was 29.6136 nmol per g dry weight (cf. FIG. 9).

e) Determination of ADP showed behavior similar to that with ATP. However, the ADP concentrations remained substantially stable on use of HES. The large decrease in the ADP concentration after deswelling by use of dextran was significant by comparison with the ADP concentration after storage without deswelling. In contrast thereto, deswelling by use of HES showed no significant deterioration. The ADP content on use of HES was 104.3943±117.6315 nmol per g dry weight and that on use of dextran was 39.4678±48.8060 nmol per g dry weight (cf. FIG. 9).

f) Unlike the high-energy adenosine phosphates, there was an increase in AMP on deswelling by use of HES. The difference is statistically significantly different both by comparison with the deswelling by use of dextran and by comparison with the values before deswelling. The value on use of HES was 58.8233±46.5900 nmol per g dry weight and that on use of dextran was 32.0286±47.4505 nmol per g dry weight (cf. FIG. 9).

g) Total of all phosphates (i.e. total of ATMP+ADP+AMP):

The values found before and after the deswelling by use of HES were approximately the same, whereas, by contrast, the high-energy phosphates were significantly reduced after deswelling by the use of dextran. The difference between the values for the deswelling by use of HES and for the deswelling by use of dextran was likewise significant. The value on use of HES was 280.6866±294.1184 nmol per g dry weight and that on use of dextran was 101.1101±124.0265 nmol per g dry weight (cf. FIG. 10).

h) Adenylate Energy Charge:

The energy status does not differ significantly in the three groups. The value on use of HES was 0.55±0.16 and that on use of dextran was 0.65±0.16 (cf. FIG. 11).

FIGS. 6 to 11 additionally show the means±standard deviation before the deswelling as comparison values.

What is claimed is:

1. A composition for the deswelling of corneas in organ culture, comprising a culture medium and a deswelling substance, wherein the deswelling substance is hydroxyethylstarch with an average molecular weight $M_w$ of from 70,000 to 200,000, with a degree of substitution MS of from 0.15 to 0.5, with a degree of substituting DS of from 0.15 to 0.5 and with a ratio of substitution at C2 to substitution at C6 of the anhydroglucose units of $\geq 8$.

2. A composition as claimed in claim 1, wherein the average molecular weight $M_w$ is from 100,000 to 160,000, the degree of substitution MS is from 0.2 to 0.45, the degree of substitution DS is from 0.2 to 0.4 and the ratio of substitution at C2 to substitution at C6 of the anhydroglucose units is from 8 to 20.

3. A composition as claimed in claim 2, wherein the average molecular weight $M_w$ is 130,000±20,000, the degree of substitution MS is from 0.38 to 0.45, the degree of substitution DS is from 0.32 to 0.40 and the ratio of substitution at C2 to substitution at C6 of the anhydroglucose units is from 8 to 20.

4. A composition as claimed in claim 1, which is used in the organ culture of human corneas.

5. A composition as claimed in claim 1, wherein the hydroxyethylstarch is used in a concentration of from 1 to 20% (weight/volume).

6. A composition as claimed in claim 5, wherein the concentration is from 2 to 15% (weight/volume).

7. A composition as claimed in claim 6, wherein the concentration is from 5 to 10% (weight/volume).

8. A composition as claimed in claim 7, wherein the concentration is 7.5% (weight/volume).

9. A method of deswelling corneas comprising contacting the corneas with the composition of claim 1.

* * * * *